(12) United States Patent
Heldreth et al.

(10) Patent No.: US 11,324,600 B2
(45) Date of Patent: *May 10, 2022

(54) TIBIAL TRAY WITH FIXATION FEATURES

(71) Applicant: DEPUY IRELAND UNLIMITED COMPANY, Ringaskiddy (IE)

(72) Inventors: Mark A. Heldreth, Mentone, IN (US); Danny W. Rumple, Jr., Warsaw, IN (US); Alyssa M. Haines, Fort Wayne, IN (US); J. Bohannon Mason, Charlotte, NC (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 121 days.

This patent is subject to a terminal disclaimer.

(21) Appl. No.: 16/430,852

(22) Filed: Jun. 4, 2019

(65) Prior Publication Data
US 2019/0282368 A1 Sep. 19, 2019

Related U.S. Application Data

(63) Continuation of application No. 15/590,537, filed on May 9, 2017, now Pat. No. 10,307,260.

(51) Int. Cl.
*A61F 2/38* (2006.01)
*A61F 2/30* (2006.01)
*A61B 17/88* (2006.01)

(52) U.S. Cl.
CPC .......... *A61F 2/389* (2013.01); *A61B 17/8802* (2013.01); *A61F 2/30767* (2013.01); *A61F 2002/308* (2013.01); *A61F 2002/3081* (2013.01); *A61F 2002/3082* (2013.01); *A61F 2002/30321* (2013.01); *A61F 2002/30733* (2013.01); *A61F 2002/30805* (2013.01); *A61F 2002/30808* (2013.01); *A61F 2002/30878* (2013.01); *A61F 2002/30884* (2013.01)

(58) Field of Classification Search
CPC .................. A61F 2/389; A61F 2/30767; A61F 2002/3082; A61F 2002/30805; A61F 2002/30321; A61F 2/38
See application file for complete search history.

(56) References Cited

U.S. PATENT DOCUMENTS

| | | | |
|---|---|---|---|
| 4,938,769 A * | 7/1990 | Shaw | A61F 2/3845 623/20.15 |
| 5,152,797 A | 10/1992 | Luckman et al. | |
| 5,826,586 A | 10/1998 | Mishra et al. | |
| 6,500,208 B1 | 12/2002 | Metzger et al. | |
| 8,475,536 B2 | 7/2013 | Tong et al. | |
| 10,307,260 B2 | 6/2019 | Heldreth et al. | |
| 2009/0088859 A1 | 4/2009 | Hazebrouck et al. | |
| 2016/0278929 A1 | 9/2016 | Harris et al. | |

OTHER PUBLICATIONS

European Search Report, European Application No. 18171207.6-1122, dated Sep. 24, 2018, 9 pages.

* cited by examiner

*Primary Examiner* — Brian A Dukert
(74) *Attorney, Agent, or Firm* — Barnes & Thornburg LLP (57) ABSTRACT

An orthopaedic prosthesis including a tibial tray is disclosed. The tibial tray includes a distal pocket and a plurality of inner pockets. Each inner pocket includes a channel sized to receive bone cement. The tibial tray includes distal-facing surfaces that have a surface roughness (Ra) equal to about 5.0 microns.

19 Claims, 6 Drawing Sheets

TIBIAL TRAY WITH FIXATION FEATURES

This application is a continuation application and claims priority to U.S. patent application Ser. No. 15/590,537, now U.S. Pat. No. 10,307,260, which was filed on May 9, 2017, the entirety of which is expressly incorporated herein by reference.

TECHNICAL FIELD

The present disclosure relates generally to orthopaedic prostheses, and particularly to orthopaedic prostheses for use in knee replacement surgery.

BACKGROUND

During the lifetime of a patient, it may be necessary to perform a joint replacement procedure on the patient as a result of, for example, disease or trauma. The joint replacement procedure may involve the use of a prosthetic implant, which is secured to one or more of the patient's bones. In the case of a knee replacement procedure, the prosthetic implant may be an assembly or system that includes a femoral component that is configured to be attached a surgically-prepared distal end of the patient's femur and a tibial tray component that is attached to a surgically-prepared proximal end of the patient's tibia. The prosthetic implant assembly may also include an insert component that is secured to the tibial tray component. Curved surfaces of the femoral component engage the insert component, and the interaction between the femoral component, the insert component, and the tibial tray component affect the resulting range of motion of the patient's knee.

The tibial tray component and the femoral component are typically fixed to the patient's tibia and patient's femur, respectively, through the use of bone cement. In the case of the tibial tray component, the bone cement is positioned between portions of the tibial tray component and a surgically-prepared surface of the proximal end of the patient's tibia. It has been found that the intra-operative presence of lipids and marrow, especially when combined with intra-operative motion of the tibial tray during implantation, can result in the infiltration of lipids and marrow into the implant/cement interface. The result can be a significant reduction in the fixation strength between the tibial tray and the bone cement.

SUMMARY

According to one aspect, an orthopaedic prosthesis including a tibial tray is disclosed. The tibial tray includes a distal-facing pocket and a plurality of inner pockets that are positioned in the distal-facing pocket. Each inner pocket includes a channel that is sized to receive bone cement. The tibial tray also includes distal-facing surfaces that have a surface roughness (Ra) of about 5.0 microns.

According to another aspect of the disclosure, an orthopaedic prosthetic component is disclosed. The prosthetic component comprises a plate including a distal surface and an elongated stem extending from the distal surface of the plate to a distal tip. The plate also includes a distal-facing opening defined in the distal surface, a proximal surface configured to receive an insert component, and a curved outer wall extending between the distal surface and the proximal surface.

The plate further includes an intermediate wall positioned between the proximal surface and the distal surface, and an inner wall that extends inwardly from the distal-facing opening to the intermediate wall to define a distal pocket. The plate further includes a plurality of inner pockets in the intermediate wall, and each inner pocket is defined by a base wall that is positioned proximal of the intermediate wall and a rim wall that extends between an opening in the intermediate wall and the base wall. Each inner pocket includes an annular channel positioned between the intermediate wall and the base wall. The distal surface and the intermediate wall have a surface roughness (Ra) in a range of 3.5 microns to 6.5 microns.

In some embodiments, the plurality of inner pockets may include an anterior pocket and a posterior pocket positioned posterior of the anterior pocket. Additionally, in some embodiments, the anterior pocket may be one of a plurality of anterior pockets, and the posterior pocket may be one of a plurality of posterior pockets. In some embodiments, each anterior pocket may be larger than each posterior pocket.

In some embodiments, the orthopaedic prosthetic component further comprises a medial keel connected to the elongated stem and the distal surface of the plate and positioned between a first anterior pocket and a first posterior pocket, and a lateral keel connected to the elongated stem and the distal surface of the plate and positioned between a second anterior pocket and a second posterior pocket.

In some embodiments, at least a portion of each base wall may have a surface roughness (Ra) of about 5.0 microns. Additionally, in some embodiments, at least a portion of each base wall may have a surface roughness (Ra) in a range of 3.5 microns to 6.5 microns.

In some embodiments, each rim wall may include a convex distal surface and a concave proximal surface that cooperate to define the annular channel. Additionally, in some embodiments, each inner pocket may include a narrowest opening extending parallel to the base wall of the inner pocket that is defined by the convex distal surface of the rim wall, and the narrowest opening of the inner pocket may have a surface area that is less than the surface area of the base wall of the inner pocket.

In some embodiments, an imaginary line on the convex distal surface defines a peripheral edge of the narrowest opening of each inner pocket. The peripheral edge may have a peripheral edge length and may define a surface area of the narrowest opening of the inner pocket. The plate may have a total peripheral edge length that is equal to the sum of the peripheral edge lengths of the plurality of inner pockets, and the plate may have a total opening surface area that is equal to the sum of the surface areas of the narrowest openings of the plurality of inner pockets. A ratio of the total peripheral edge length to the total opening surface area may be greater than 0.20. In some embodiments, the ratio of the total peripheral edge length to the total inner opening surface area may be in a range of 0.31 to 0.46.

In some embodiments, the proximal surface of the plate may include a buttress configured to engage the insert component.

Additionally, in some embodiments, the inner wall that defines the distal pocket may include multiple interconnected curved surfaces. In some embodiments, the elongated stem may include an outer surface having a surface roughness (Ra) in a range of 3.5 microns to 6.5 microns.

According to another aspect, an orthopaedic prosthesis comprises a tibial tray including a distal surface and an opening is defined in the distal surface. The tibial tray includes an inner wall extending inwardly from the opening to an intermediate wall to define a first pocket in the tibial tray. The intermediate wall includes a plurality of second openings, and a rim wall extends inwardly from each second opening to a base wall to define a plurality of inner pockets in the tibial tray. Each inner pocket includes a central recess and an undercut channel. The distal surface and the intermediate wall have a surface roughness (Ra) greater than or equal to 3.5 microns.

In some embodiments, the orthopaedic prosthesis may further comprise an insert component having a pair of concave curved surfaces configured to articulate with corresponding convex curves surfaces of a femoral component. The tibial tray may include a proximal buttress configured to engage the insert component.

In some embodiments, the tibial tray may include an elongated stem and a pair of keels extending from the distal surface. Additionally, in some embodiments, a first keel of the pair of keels may be positioned between a first anterior inner pocket and a first posterior inner pocket of the plurality of inner pockets, and a second keel of the pair of keels may be positioned between a second anterior inner pocket and a second posterior inner pocket of the plurality of inner pockets. In some embodiments, each of the first anterior inner pocket and the second anterior inner pocket may be larger than either of the first and second posterior inner pockets.

In some embodiments, each rim wall may include a convex distal surface and a concave proximal surface that cooperate to define the undercut channel.

In some embodiments, the distal surface and the intermediate wall may have a surface roughness (Ra) of equal to about 5.0 microns. Additionally, in some embodiments, the distal surface and the intermediate wall may have a surface roughness (Ra) of less than 6.5 microns.

According to another aspect, an orthopaedic prosthetic component comprises a tibial tray including a distal surface and an opening is defined in the distal surface. The tibial tray includes a first wall extending inwardly from the opening to a second wall to define a first pocket in the tibial tray. The second wall includes a plurality of second openings, and a third wall extends inwardly from each second opening to a fourth wall to define a plurality of inner pockets in the tibial tray. Each inner pocket including an undercut channel. The distal surface and the second wall have a surface roughness (Ra) greater than or equal to 3.5 microns. In some embodiments, the distal surface and the second wall may have a surface roughness (Ra) equal to about 5.0 microns.

In some embodiments, at least a portion of each fourth wall may have a surface roughness (Ra) that is greater than or equal to 3.5 microns. Additionally, in some embodiments, each fourth wall may have a surface roughness (Ra) that is equal to about 5.0 microns. In some embodiments, each fourth wall may have a surface roughness (Ra) that is less than or equal to 6.5 microns.

Additionally, in some embodiments, each third wall may include a convex distal surface and a concave proximal surface that cooperate to define the undercut channel.

In some embodiments, each inner pocket may have an inner peripheral edge that is defined by an imaginary line on its third wall and the inner peripheral edge may have a peripheral edge length. The plate may have a total peripheral edge length that is equal to the sum of the peripheral edge lengths of the plurality of inner pockets, and the plate may have a total opening surface area that is equal to the sum of the surface areas of the narrowest openings of the plurality of inner pockets. A ratio of the total peripheral edge length to the total opening surface area may be greater than 0.20 and less than 0.46.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
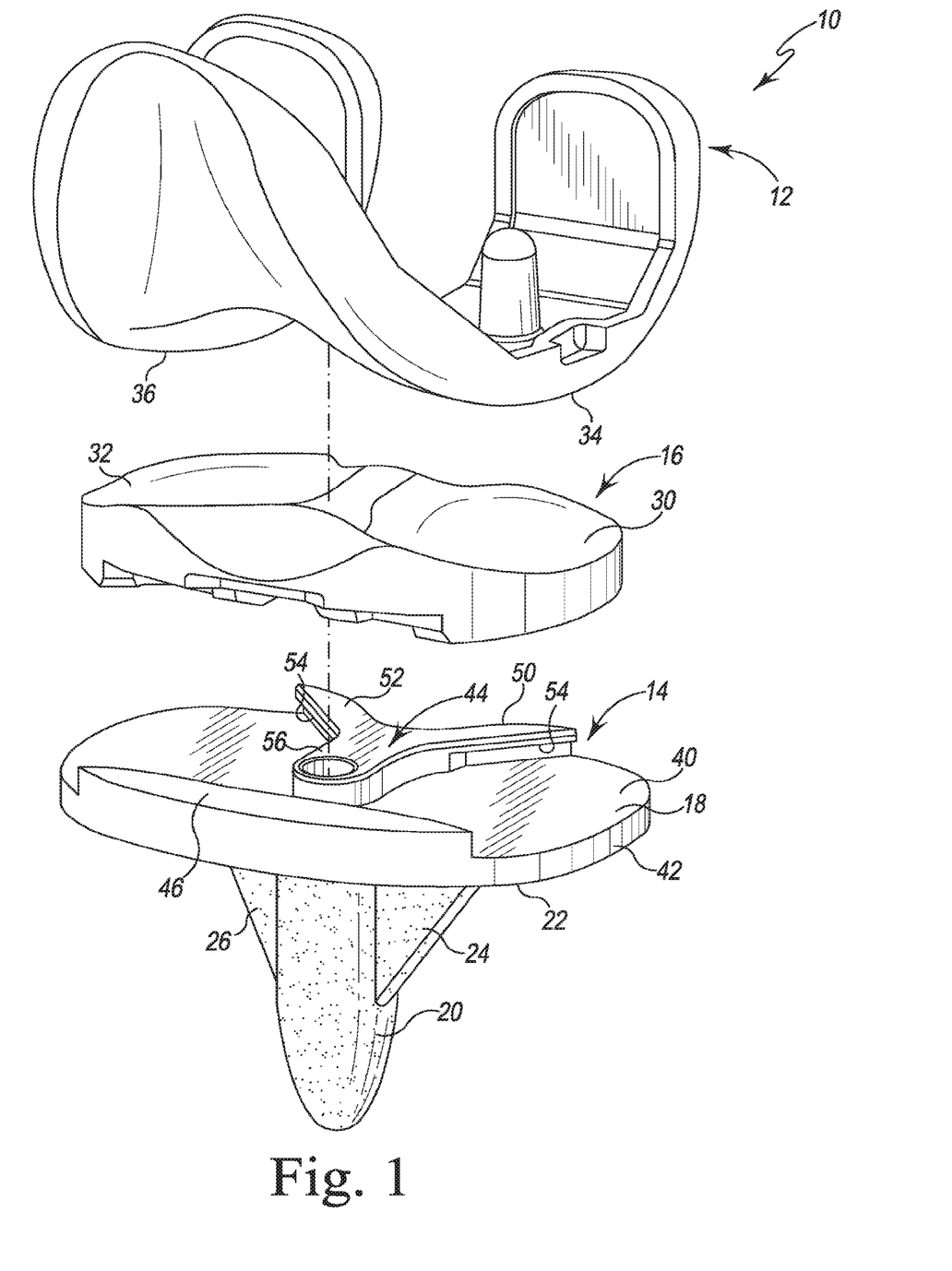
FIG. 1 is a perspective view of an orthopaedic prosthesis.

Referring now to FIG. 1, a fixed-bearing knee prosthesis 10 is shown. The knee prosthesis 10 includes a femoral component 12, a tibial tray component 14, and an insert component 16. The tibial tray 14 includes a plate or platform 18 and an elongated stem 20 that extends away from the distal surface 22 of the platform 18. A medial keel 26 and a lateral keel 24 are attached to the distal surface 22 of the platform 18 and extend along a portion of the elongated stem 20. The elongated tibial stem 20 and the keels 24, 26 are configured to be implanted into a surgically-prepared proximal surface 152 of a patient's tibia 150 (see FIG. 5). It should be appreciated that other fixation members, such as one or more short pegs or posts, may be used in lieu of the elongated stem 20. In the illustrative embodiment, the elongated stem includes an outer surface having a surface roughness (Ra) in a range of 3.5 microns to 6.5 microns.

The insert component 16 is securable to the tibial tray 14 via a snap-fit. In such a way, the insert 16 is fixed relative to the tibial tray 14 (i.e., it is not rotatable or moveable in the anterior/posterior or medial/lateral directions). The insert 16 includes a lateral bearing surface 30 and a medial bearing surface 32. The bearing surfaces 30, 32 are concave and curved to articulate with a convex curved lateral condyle surface 34 and a convex curved medial condyle surface 36, respectively, of the femoral component 12.

The femoral component 12 is configured to be implanted into a surgically prepared end of the patient's femur (not shown), and is configured to emulate the configuration of the patient's natural femoral condyles. As such, the lateral condyle surface 34 and the medial condyle surface 36 are configured (e.g., curved) in a manner which mimics the condyles of the natural femur. The lateral condyle surface 34 and the medial condyle surface 36 are spaced apart from one another thereby defining an intercondylar notch therebetween.

The components of the knee prosthesis 10 that engage the natural bone, such as the femoral component 12 and the tibial tray 14, may be constructed with a biocompatible metal, such as a cobalt chrome alloy, although other materials may also be used. The bone engaging surfaces of these components may be textured to facilitate cementing the component to the bone, as described in greater detail below. Such surfaces may also be porous coated to promote bone ingrowth for permanent fixation.

The insert 16 may be constructed with a material that allows for smooth articulation between the bearing 16 and the femoral component 12, such as a polymeric material. One such polymeric material is polyethylene such as ultra-high molecular weight polyethylene (UHMWPE).

As shown in FIG. 1, the tibial tray 14 includes a proximal surface 40 that is positioned opposite the distal surface 22 and a curved outer wall 42 that extends between the surfaces 22, 40. The proximal surface 40 configured to receive the insert 16, and, in the illustrative embodiment, includes buttresses 44, 46 that are configured to engage tabs or flanges (not shown) of the insert 16. As shown in FIG. 1, the buttress 44 has a pair of arms 50, 52 that extend along a posterior section of the perimeter of tibial tray's platform 18. Each of the arms 50, 52 includes an undercut 54 that receives one of the tabs of the insert 16. A third arm 56 of the buttress 44 extends anteriorly away from the intersection of the lateral arm 50 and the medial arm 52 (i.e., in a direction toward the center of the platform 18).

Figure 2:
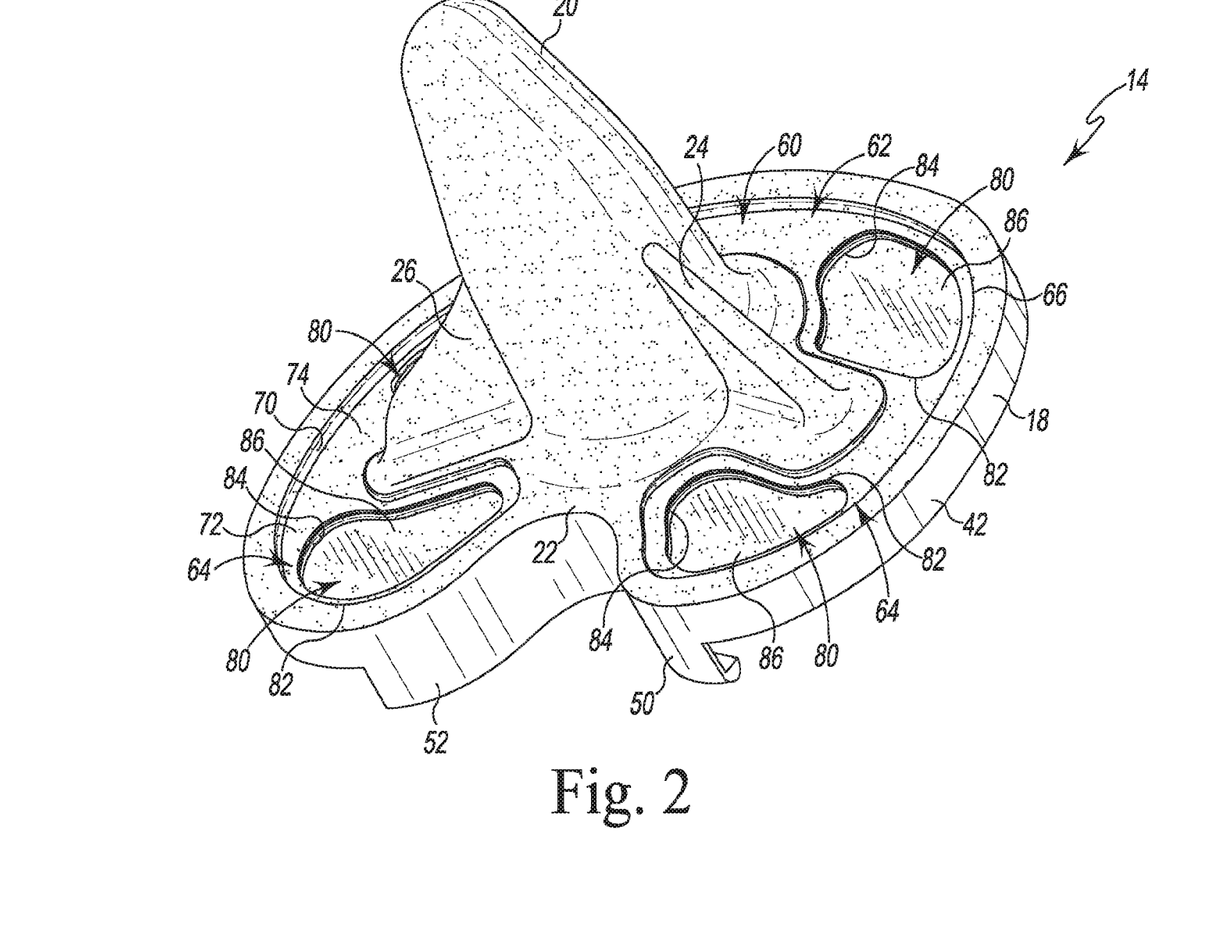
FIG. 2 is a distal perspective view of a tibial tray component of the orthopaedic prosthesis of FIG. 1.

Referring now to FIG. 2, the tibial tray 14 includes a distal pocket 60 in the distal surface 22. In the illustrative embodiment, the pocket 60 extends around the keels 24, 26 and the elongated stem 20 such that it has an anterior section 62 and two posterior sections 64. It should be appreciated that in other embodiments the pocket 60 may be divided into multiple distal pockets. The pocket 60 has a distal-facing opening 66 defined in the distal surface 22. An inner wall 70 extends inwardly (or proximally) from the opening 66 to an intermediate wall 72 of the tibial tray to define the pocket 60. The inner wall 70 includes multiple curved surfaces that interconnected and surround the pocket 60.

In the illustrative embodiment, the intermediate wall 72 includes a distal-facing surface 74 that extends parallel to the distal surface 22 of the tray 14. Each of the surfaces 22, 74 is a substantially planar surface. As used herein, the term "substantially planar" should be understood to describe a feature that is flat within the tolerances that are achievable in a typical manufacturing process. Each of the surfaces 22, 74 also has a surface roughness (Ra) in a range of 3.5 microns to 6.5 microns. In other embodiments, the surface roughness (Ra) may be greater than or equal to 3.5 microns and less than or equal to 6.5 microns. In still other embodiments, the surface roughness may be about 5 microns. As used herein, the term "about" should be understood to refer to a measurement that is within the tolerances that are achievable in a typical manufacturing process. For example, in the case of surface roughness (Ra), a typical manufacturing tolerance may be 1.5 microns.

As shown in FIG. 2, the tibial tray 14 includes a plurality of inner pockets 80, which are defined in the intermediate wall 72. Each pocket 80 is fluidly connected to the distal pocket 60 such that bone cement may enter the pockets 60, 80 during implantation, as described in greater detail below. Each pocket 80 has a distal-facing opening 82 defined in the intermediate wall 72. A rim wall 84 extends inwardly (or proximally) from the opening 82 to the base wall 86 to define each pocket 80, as described in greater detail below. The base wall 86 is substantially planar and extends parallel to the distal surface 22 and the intermediate wall 72 in the illustrative embodiment.

Figure 3:
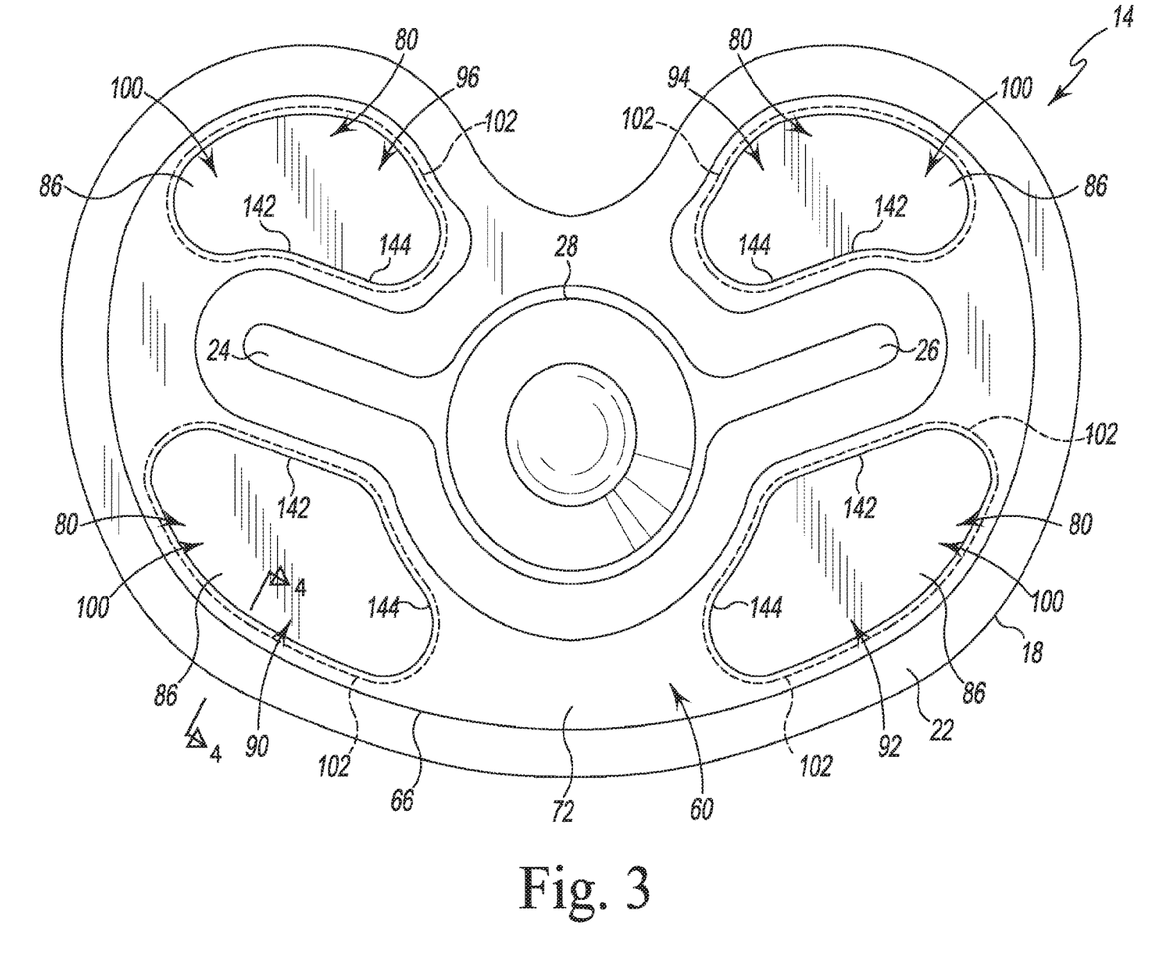
FIG. 3 is a distal plan view of the tibial tray component of FIGS. 1-2 with the surface treatment removed for ease of viewing.

As shown in FIG. 3, the inner pockets 80 include a pair of anterior pockets 90, 92, which are positioned anterior of the keels 24, 26, respectively, and a pair of posterior pockets 94, 96, which are positioned posterior of the keels 24, 26 (and hence the pockets 90, 92), respectively. As shown in FIG. 3, configuration of the anterior pocket 90 mirrors that of the anterior pocket 92. Similarly, the configuration of the posterior pocket 94 mirrors that of the posterior pocket 96. In the illustrative embodiment, the anterior pockets 90, 92 are larger than the posterior pockets 94, 96. It should be appreciated that in other embodiment the configuration of the pockets may vary depending on, among other things, the location and geometries of the stem 20, the keels 26, 24, and the platform 18.

In the illustrative embodiment, each inner pocket 80 has a central recess 100 and an annular undercut or channel 102 (shown in broken line in FIG. 3) that extends around the perimeter 104 (see FIG. 4) of the recess 100. The portion of the base wall 86 of each pocket 80 defining the central recess 100 has a surface roughness (Ra) in a range of 3.5 microns to 6.5 microns. In other embodiments, the surface roughness (Ra) may be greater than or equal to 3.5 microns and less than about 6.5 microns. It should also be appreciated that other portions of the base wall 86 and the rim wall 84 of each pocket 80 may also have a surface roughness (Ra) in a range of 3.5 microns to 6.5 microns.

Figure 4:
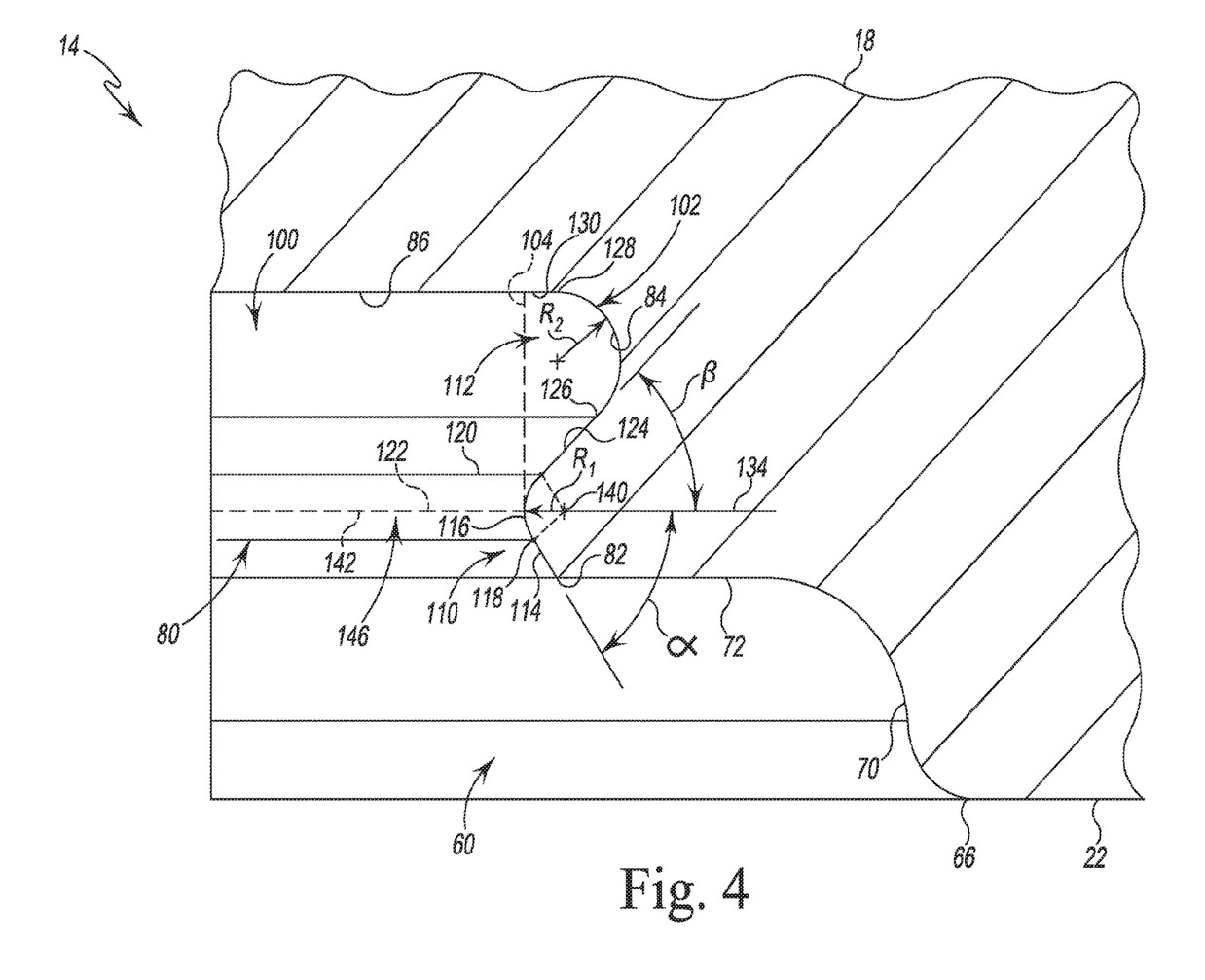
FIG. 4 is a partial cross-sectional elevation view of the tibial tray component of FIGS. 1-3 taken along the line 4-4 in FIG. 3 and oriented such that the distal surface is facing toward the bottom edge of the illustration.

As described above, the distal pocket 60 of the tibial tray has a distal-facing opening 66 defined in the distal surface 22 of the platform 18. As shown in FIG. 4, an inner wall 70 extends inwardly (or proximally) from the opening 66 to an intermediate wall 72 to define the pocket 60. Each inner pocket 80 has a distal-facing opening 82 defined in the intermediate wall 72. The rim wall 84 of each pocket 80 extends inwardly (or proximally) from the opening 82 to the base wall 86.

In the illustrative embodiment, the rim wall 84 of each pocket 80 includes a convex surface 110 that extends inwardly from the opening 82. The rim wall 84 also includes a concave surface 112 that is connected to the convex surface 110 and the base wall 86. As shown in FIG. 4, the convex surface 110 includes a distal section 114 that extends along a straight line when the tibial tray 14 is viewed in a cross-sectional plane extending perpendicular to the distal surface 22. The distal section 114 is connected to a curved surface section 116 at an edge 118.

The curved surface section 116 has a constant radius of curvature R1 in the illustrative embodiment. The radius of curvature R1 is equal to about 0.15 millimeters but in other embodiments may be increased or decreased. It still other embodiments the radius of curvature may vary. As described in greater detail below, the curved surface section 116 of each rim wall 84 defines an inner-most edge 122 (shown in broken line in FIG. 4) of its inner pocket 80. The curved surface section 116 is connected to a proximal section 124 of the rim wall 84 at an edge 120.

As shown in FIG. 4, the proximal rim wall section 124 extends along a straight line when the tibial tray 14 is viewed in a cross-sectional plane extending perpendicular to the distal surface 22. The rim wall section 124 extends proximally to another edge 126, where it connects to the concave surface 112 of the rim wall 84. The concave surface 112 connects to the base wall 86 of each pocket 80 at an edge 128. In the illustrative embodiment, the curved surface section 116, the proximal rim wall section 124, the concave surface 112, and an outer section 130 of the base wall 86 cooperate to define the undercut channel 102 of each pocket 80. The undercut channel 102 is sized to receive bone cement during implantation to create an interlock between the tibial tray 14 and the bone cement to assist with fixation of the tibial tray 14 to the patient's tibia.

In the illustrative embodiment, the concave surface 112 has a constant radius of curvature R2. The radius of curvature R2 is equal to about 0.25 millimeters but in other embodiments may be increased or decreased. It still other embodiments the radius of curvature may vary. As shown in the cross-sectional illustration of FIG. 4, an angle α is defined between the distal rim wall section 114 and an imaginary plane 134 extending parallel to the distal surface 22. In the illustrative embodiment, the angle α is equal to about 60 degrees. It should be appreciated that in other embodiments the angle α may be about 45 degrees. An angle β is defined between the proximal rim wall section 124 and the plane 134. In the illustrative embodiment, the angle β is equal to about 45 degrees. Additionally, in the illustrative embodiment, the curved surface section 116 extends along an arc between the edges 118, 120 of about 75 degrees.

As described above, the curved surface section 116 of each rim wall 84 includes an inner-most edge 122 of its inner pocket 80. In the illustrative embodiment, the inner-most edge 122 is positioned about 60 degrees along the arc of the curved surface section 116 and lies in the plane 134 extending through the origin 140 of the radius of curvature R1. The inner-most edge 122 defines the peripheral edge of the narrowest opening 142 of each inner pocket 80, which, in the illustrative embodiment, includes the perimeter 104 of the central recess 100. Each edge 122 extends a length 144 around the outer perimeter of the recess 100 and defines a surface area 146 of each opening 142. Tables 1-2 below identifies the lengths 144 and surface areas 146 for the pockets 90, 92, 94, 96 of one embodiment.

TABLE 1

| Anterior Pocket 90 | | Posterior Pocket 94 | |
|---|---|---|---|
| Length 144 (mm) | Surface Area 146 (mm²) | Length 144 (mm) | Surface Area 146 (mm²) |
| 29.73 | 66.74 | 27.74 | 59.18 |

TABLE 2

| Anterior Pocket 92 | | Posterior Pocket 96 | |
|---|---|---|---|
| Length 144 (mm) | Surface Area 146 (mm²) | Length 144 (mm) | Surface Area 146 (mm²) |
| 29.73 | 66.74 | 27.74 | 59.18 |

In the illustrative embodiment, the sum of all of the lengths 144 is equal to 114.94 mm, and the sum of all of the surface areas 146 is equal to 251.84 mm². The ratio of the sum of all of the lengths 144 to all of the surface areas 146 is equal to 0.46. In other embodiments, the ratio may be greater than 0.20. In still other embodiments, the ratio may be in a range of 0.31 to 0.46. It has been determined that this ratio affects the balance between the shear strength of the bone cement captured under the rim walls 84 of the inner pockets 80 and the tensile strength of the cement "islands" formed in the narrowest openings 82 of the inner pockets 80. For example, if the ratio is too high (e.g., the sum of the areas is only slightly greater than the sum of the lengths 144), then the benefit of the interlock fixation provided by capturing the bone cement under the rim walls 84 will be limited by the reduced cement/bone fixation area for the "islands" of bone cement created at the narrowest openings 82. If the ratio is too low (e.g., the sum of the areas is much greater than the sum of the lengths 144), then the potential for interlock fixation with the rim wall 84 may not be achieved.

As described above, the base wall 86 of each pocket 80 has an edge 128 at which it connects to the rim wall 84. The base wall 86 has a surface area defined within the edge 128 that is greater than the surface area 146 of the narrowest opening 142 of the pocket 80. In the illustrative embodiment, the surface area defined within the edge 128 is about 261.65 mm². In other embodiments, it may be a range of 261.65 mm² to 1670.00 mm².

Figure 5:
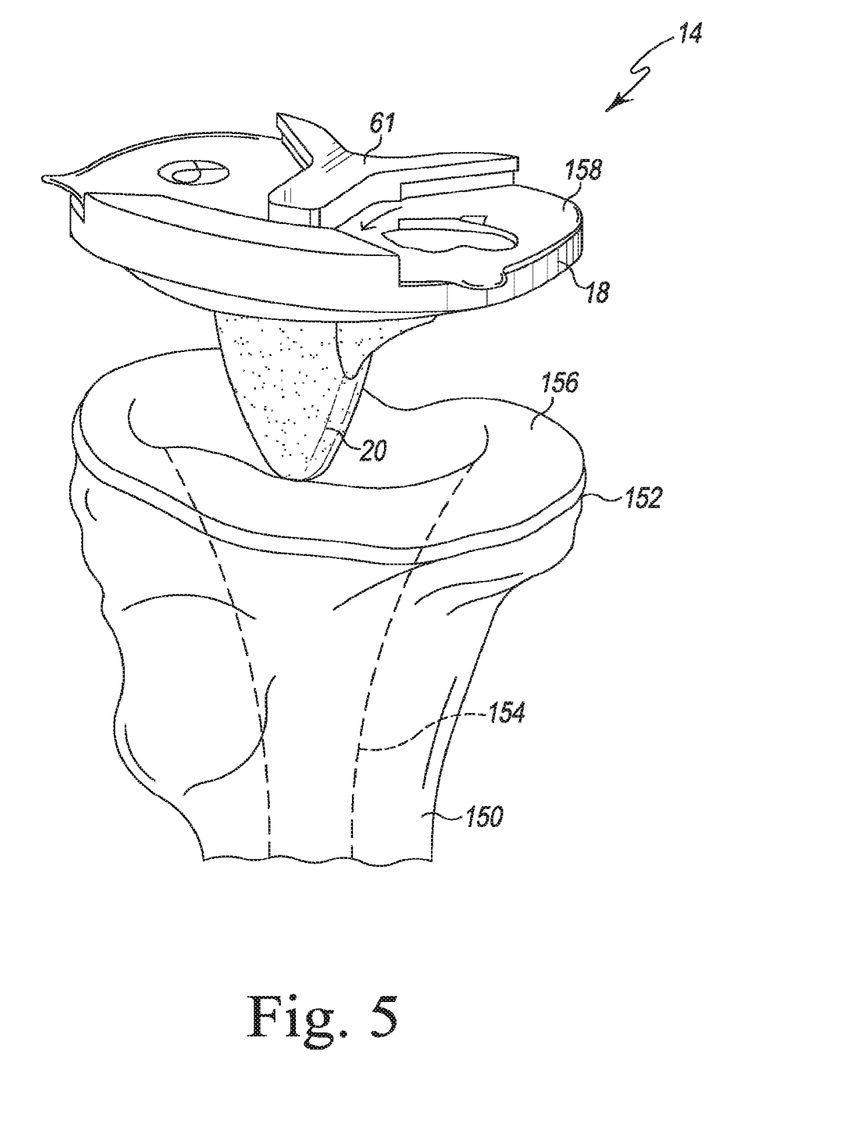
FIG. 5 is a perspective view illustrating the tibial tray component of FIGS. 1-4 positioned for implantation into a patient's surgical-prepared tibia.

Referring now to FIG. 5, the tibial tray 14 is shown positioned for implantation into the patient's tibia 150. During a surgical procedure, an orthopaedic surgeon may use one or more instruments to define a surgically-prepared proximal surface 152 to receive the platform 18 of the tibial tray 14. The orthopaedic surgeon also defines a proximal bore 154 that is sized to receive the elongated stem 20 and the keels 24, 26 of the tibial tray. After preparing the surface 152, the surgeon may apply a layer 156 of bone cement to the surface 152 in advance of positioning the tibial tray 14 as shown in FIG. 5. Additionally, in the illustrative embodiment, the proximal surface of tibial tray 14 is covered with a protective coating 158 to protect the mating features during implantation.

Figure 6:
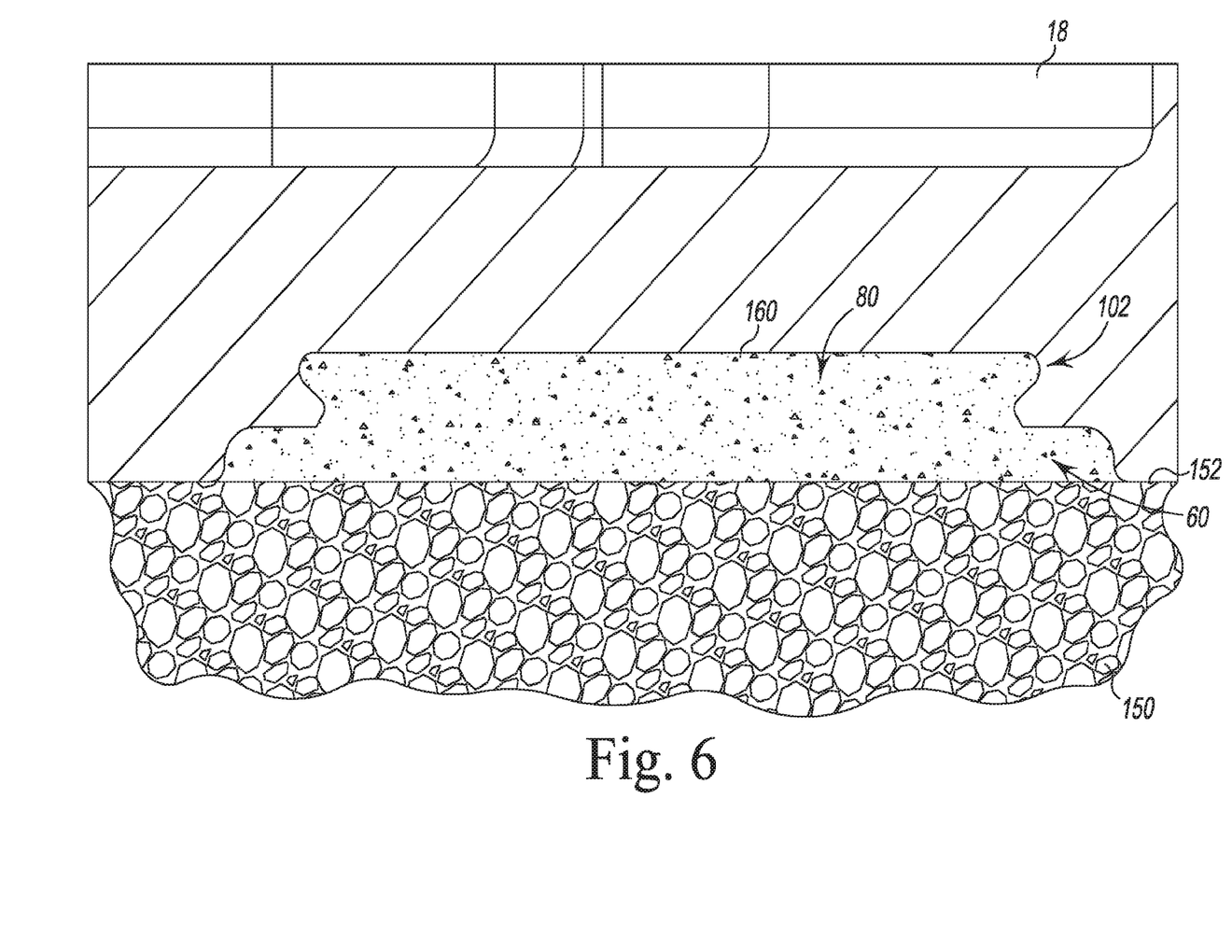
FIG. 6 is a partial cross-sectional elevation view of the tibial tray component when positioned on the patient's surgical-prepared tibia.

With the tray 14 positioned as shown in FIG. 5, the surgeon may advance the tray 14 distally to insert the stem 20 and the keels 24, 26 into the proximal bore 154. The platform 18 is advanced into contact with the cement layer 156, and the cement advances upward or proximally into the pockets 60, 80 of the tibial tray 14. As shown in FIG. 6, when the tray 14 is seated, cement 160 fills the pockets 60, 80, including the undercut channel 102, thereby creating an interlock between the tray 14 and the cement 160 and "islands" of bone cement in the narrowest openings 82 of the pockets 80. Additionally, the surface roughness of the distal surface 22, the intermediate wall 72, and the base wall 86 has been unexpectedly shown to inhibit infiltration of lipid/marrow during surgery, thereby offering increasing initial fixation between the tibial tray 14 and the cement 160.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic prosthetic component, comprising:
a plate including a distal surface, a distal-facing opening defined in the distal surface, a proximal surface configured to receive an insert component, and a curved outer wall extending between the distal surface and the proximal surface, and
an elongated stem extending from the distal surface of the plate to a distal tip,
wherein the plate further includes an intermediate wall positioned between the proximal surface and the distal surface, and an inner wall that extends inwardly from the distal-facing opening to the intermediate wall to define a distal pocket,
wherein the plate further includes a plurality of inner pockets in the intermediate wall, each inner pocket being defined by a planar base wall that is positioned proximal of the intermediate wall and a rim wall that extends between an opening in the intermediate wall and the planar base wall, wherein the rim wall includes a convex distal surface and a concave proximal surface that cooperate to define an annular channel positioned between the intermediate wall and the base wall, wherein the convex distal surface includes a curved surface section having an arc length defined by a radius of curvature and an inner-most edge and wherein the curved surface section defines a surface area of the convex distal surface and the length of the inner-most edge defines a length of the curved surface section, and
wherein the distal surface and the intermediate wall have a surface roughness (Ra) in a range of 3.5 microns to 6.5 microns.

2. The orthopaedic prosthetic component of claim 1, wherein the plurality of inner pockets includes an anterior pocket and a posterior pocket positioned posterior of the anterior pocket.

3. The orthopaedic prosthetic component of claim 2, wherein the anterior pocket is one of a plurality of anterior pockets and the posterior pocket is one of a plurality of posterior pockets.

4. The orthopaedic prosthetic component of claim 3, further comprising:
a medial keel connected to the elongated stem and the distal surface of the plate and positioned between a first anterior pocket and a first posterior pocket, and
a lateral keel connected to the elongated stem and the distal surface of the plate and positioned between a second anterior pocket and a second posterior pocket.

5. The orthopaedic prosthetic component of claim 3, wherein each anterior pocket is larger than each posterior pocket.

6. The orthopaedic prosthetic component of claim 1, wherein at least a portion of each planar base wall has a surface roughness (Ra) in a range of 3.5 microns to 6.5 microns.

7. The orthopaedic prosthetic component of claim 1, wherein each inner pocket includes:

a narrowest opening extending parallel to the planar base wall of the inner pocket that is defined by the convex distal surface of the rim wall, and
the narrowest opening of the inner pocket has a surface area that is less than the surface area of the planar base wall of the inner pocket.

8. The orthopaedic prosthetic component of claim 7, wherein:
an imaginary line on the convex distal surface defines a peripheral edge of the narrowest opening of each inner pocket, the peripheral edge having a peripheral edge length and defining a surface area of the narrowest opening of the inner pocket,
the plate has a total peripheral edge length that is equal to the sum of the peripheral edge lengths of the plurality of inner pockets, and the plate has a total opening surface area that is equal to the sum of the surface areas of the narrowest openings of the plurality of inner pockets, and
a ratio of the total peripheral edge length to the total opening surface area is greater than 0.20 and less than 0.50.

9. The orthopaedic prosthetic component of claim 8, wherein the ratio of the total peripheral edge length to the total inner opening surface area is in a range of 0.31 to 0.46.

10. The orthopaedic prosthetic component of claim 1, wherein the proximal surface of the plate includes a buttress configured to engage the insert component.

11. The orthopaedic prosthetic component of claim 1, wherein the inner wall that defines the distal pocket includes multiple interconnected curved surfaces.

12. The orthopaedic prosthetic component of claim 1, wherein the elongated stem includes an outer surface having a surface roughness (Ra) in a range of 3.5 microns to 6.5 microns.

13. An orthopaedic prosthesis, comprising:
a tibial tray including a distal surface and an opening is defined in the distal surface,
wherein the tibial tray includes an inner wall extending inwardly from the opening to an intermediate wall to define a first pocket in the tibial tray,
wherein the intermediate wall includes a plurality of second openings, and a rim wall extends inwardly from each second opening to a base wall to define a plurality of inner pockets in the tibial tray, each inner pocket including a central recess and an undercut channel, wherein each rim wall includes a concave proximal surface and a convex distal surface that cooperate to define the corresponding undercut channel, wherein the convex distal surface includes a curved surface section having an arc length defined by a radius of curvature and an inner-most edge and wherein the curved surface section defines a surface area of the convex distal surface and the length of the inner-most edge defines a length of the curved surface section,
wherein the plurality of inner pockets includes a plurality of anterior inner pockets and a plurality of posterior inner pockets, wherein each anterior inner pocket is located on the intermediate wall anteriorly of each of the posterior inner pockets and is larger than each of the posterior inner pockets, and
wherein the distal surface and the intermediate wall have a surface roughness (Ra) in a range of 3.5 microns to 6.5 microns.

14. The orthopaedic prosthesis of claim 13, further comprising:

an insert component having a pair of concave curved surfaces configured to articulate with corresponding convex curves surfaces of a femoral component, wherein the tibial tray includes a proximal buttress configured to engage the insert component.

15. The orthopaedic prosthesis of claim 13, wherein the tibial tray includes an elongated stem and a pair of keels extending from the distal surface.

16. The orthopaedic prosthesis of claim 15, wherein:

a first keel of the pair of keels is positioned between a first anterior inner pocket and a first posterior inner pocket of the plurality of inner pockets, and a second keel of the pair of keels is positioned between a second anterior inner pocket and a second posterior inner pocket of the plurality of inner pockets.

17. The orthopaedic prosthesis of claim 13, wherein at least a portion of each base wall has a surface roughness (Ra) in a range of 3.5 microns to 6.5 microns.

18. The orthopaedic prosthesis of claim 13, wherein:

each inner pocket has an inner peripheral edge that is defined by an imaginary line on its rim wall, the inner peripheral edge having a peripheral edge length, the tibial tray has a total peripheral edge length that is equal to the sum of the peripheral edge lengths of the plurality of inner pockets, and the tibial tray has a total opening surface area that is equal to the sum of the surface areas of a narrowest openings of the plurality of inner pockets, and a ratio of the total peripheral edge length to the total opening surface area is greater than 0.20 and less than 0.50.

19. The orthopaedic prosthesis of claim 18, wherein the ratio of the total peripheral edge length to the total opening surface area is in a range of 0.31 to 0.46.

* * * * *